United States Patent
Pfeiffer et al.

(10) Patent No.: US 12,239,947 B2
(45) Date of Patent: Mar. 4, 2025

(54) METHOD FOR THE PRODUCTION OF SUPERABSORBENTS

(71) Applicant: BASF SE, Ludwigshafen (DE)

(72) Inventors: Thomas Pfeiffer, Ludwigshafen (DE); Ruediger Funk, Ludwigshafen (DE); Marco Krueger, Ludwigshafen (DE); Karl Possemiers, Antwerp (BE); Juergen Schroeder, Ludwigshafen (DE); Matthias Weismantel, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 1011 days.

(21) Appl. No.: 17/264,093

(22) PCT Filed: Aug. 9, 2019

(86) PCT No.: PCT/EP2019/071450
§ 371 (c)(1),
(2) Date: Jan. 28, 2021

(87) PCT Pub. No.: WO2020/038742
PCT Pub. Date: Feb. 27, 2020

(65) Prior Publication Data
US 2021/0154637 A1  May 27, 2021

(30) Foreign Application Priority Data

Aug. 20, 2018 (EP) .................... 18189715

(51) Int. Cl.
*B01J 13/00* (2006.01)
*A61L 15/60* (2006.01)
*C08F 2/01* (2006.01)
*C08F 2/16* (2006.01)

(52) U.S. Cl.
CPC .......... *B01J 13/0069* (2013.01); *A61L 15/60* (2013.01); *B01J 13/0065* (2013.01); *C08F 2/01* (2013.01); *C08F 2/16* (2013.01)

(58) Field of Classification Search
CPC ... B01J 13/0069; B01J 13/0065; A61L 15/60; C08F 2/01; C08F 2/16
See application file for complete search history.

(56) References Cited

U.S. PATENT DOCUMENTS

| 6,241,928 B1 | 6/2001 | Hatsuda et al. |
| 2010/0099799 A1 | 4/2010 | Fricker et al. |
| 2010/0105808 A1 | 4/2010 | Fricker et al. |
| 2012/0202951 A1* | 8/2012 | Gartner ..................... C08F 4/40 525/360 |

FOREIGN PATENT DOCUMENTS

| DE | 3825366 A1 | 2/1989 |
| EP | 2371869 A1 | 10/2011 |
| WO | WO-2010040466 A1 | 4/2010 |
| WO | WO-2010040467 A1 | 4/2010 |
| WO | WO-2013120722 A1 | 8/2013 |

OTHER PUBLICATIONS

Graham, et al., "Chapter 3: Commercial Processes for the Manufacture of Superabsorbent Polymers", Modern Superabsorbent Polymer Technology, Ed. Buchholz, et al., 1998, pp. 71-117.
International Application No. PCT/EP2019/071450, International Search Report, mailed Nov. 4, 2019.

* cited by examiner

*Primary Examiner* — Daniel Berns
(74) *Attorney, Agent, or Firm* — Element IP, PLC

(57) ABSTRACT

A process for producing superabsorbent particles by polymerizing a monomer solution, comprising the steps of continuously polymerizing the monomer solution on the continuous belt of a belt reactor, comminuting the polymer gel obtained, rinsing the polymer gel obtained on the underside of the belt reactor into a separation unit with water, separating the polymer gel from the water in the separation unit and recycling the polymer gel into the comminution, wherein the polymer gel has a swelling capacity in water of at least 100 g/g, the dwell time of the polymer gel in the rinse water is less than 40 minutes, and the separation unit has openings with a clear width of at least 1 mm.

16 Claims, No Drawings

METHOD FOR THE PRODUCTION OF SUPERABSORBENTS

CROSS-REFERENCE TO RELATED APPLICATIONS

This is the U.S. national phase of International Application No. PCT/EP2019/071450, filed Aug. 9, 2019, which claims the benefit of European Patent Application No. 18189715.8, filed on Aug. 20, 2018.

The present invention relates to a process for producing superabsorbent particles by polymerizing a monomer solution, comprising the steps of continuously polymerizing the monomer solution on the continuous belt of a belt reactor, comminuting the polymer gel obtained, rinsing the polymer gel obtained on the underside of the belt reactor into a separation unit with water, separating the polymer gel from the water in the separation unit and recycling the polymer gel into the comminution, wherein the polymer gel has a swelling capacity in water of at least 100 g/g, the dwell time of the polymer gel in the rinse water is less than 20 minutes, and the separation unit has openings with a clear width of at least 1 mm.

Superabsorbents are used to produce diapers, tampons, sanitary napkins and other hygiene articles, but also as water-retaining agents in market gardening. Superabsorbents are also referred to as water-absorbing polymers.

The production of superabsorbents is described in the monograph "Modern Superabsorbent Polymer Technology", F. L. Buchholz and A. T. Graham, Wiley-VCH, 1998, pages 71 to 103.

The properties of the superabsorbents can be adjusted, for example, via the amount of crosslinker used. With increasing amount of crosslinker, the centrifuge retention capacity (CRC) falls and the absorption under a pressure of 21.0 g/cm$^2$ (AUL0.3 psi) passes through a maximum.

To improve the performance properties, for example gel bed permeability (GBP) and absorption under a pressure of 49.2 g/cm$^2$ (AUL0.7 psi), superabsorbent particles are generally surface postcrosslinked. This increases the level of crosslinking of the particle surface, which can at least partly decouple the absorption under a pressure of 49.2 g/cm$^2$ (AUL0.7 psi) and the centrifuge retention capacity (CRC). This surface postcrosslinking can be performed in the aqueous gel phase. Preferably, however, polymer particles (base polymer), having been dried, ground and sieved off, are surface coated with a surface postcrosslinker and thermally surface postcrosslinked. Crosslinkers suitable for that purpose are compounds which can form covalent bonds with at least two carboxylate groups of the polymer particles.

Production of superabsorbents on the continuous belt of a belt reactor is described, for example, in DE 38 25 366 A1 and U.S. Pat. No. 6,241,928.

It was an object of the present invention to provide an improved process for producing superabsorbents by polymerizing on the continuous belt of a belt reactor, especially improved recycling of the polymer gel obtained on the underside of the belt reactor.

The object was achieved by a process for producing superabsorbents by polymerizing a monomer solution comprising
a) at least one ethylenically unsaturated monomer which bears acid groups and has been neutralized to an extent of 50 to 85 mol %,
b) at least one crosslinker,
c) at least one initiator,
d) optionally one or more ethylenically unsaturated monomers copolymerizable with the monomers mentioned under a) and
e) optionally one or more water-soluble polymers,
comprising the steps of
i) continuously polymerizing the monomer solution on the continuous belt of a belt reactor,
ii) comminuting the polymer gel obtained in step i),
iii) rinsing the polymer gel obtained on the underside of the belt reactor into a separation unit with water,
iv) separating the polymer gel from the water in the separation unit and
v) recycling the polymer gel separated off in step iv) into step ii),
wherein the polymer gel has a swelling capacity in water of at least 100 g/g, the dwell time between step iii) and step iv) is less than 20 minutes, and the separation unit in step iv) has openings with a clear width of at least 1 mm.

The dwell time between step iii) and step iv) is preferably less than 15 minutes, more preferably less than 10 minutes, most preferably less than 5 minutes.

The dwell time here is the time between the first contact of a polymer gel particle with the rinse water and entry of the polymer gel particle into the separation unit. The system should be free of dead spaces, meaning that, with the rinse water switched off, the system should run dry between the rinse water feed and the drain from the separation unit. In this case, the dwell time can be determined by supplying a constant amount of rinse water until a steady state is attained and then stopping the supply of rinse water. The amount of rinse water that runs out of the separation unit after the supply of rinse water has been switched off is measured. Dwell time can be calculated by the following formula:

$$VWZ[\min] = x[m^3] \bigg/ y\left[\frac{m^3}{\min}\right]$$

VWZ dwell time
x rinse water that runs off after the supply has been switched off
y constant supply of rinse water The clear width of the openings is the distance between opposite sides of the opening. A clear width of at least 1 mm means that the width is never less than this value. The clear width of the openings is preferably at least 1.5 mm, more preferably at least 2 mm, most preferably at least 3 mm. The clear width should not exceed 15 mm.

The comminution can be performed with any suitable apparatus, for example with an extruder.

Water in the context of the present invention is tap water, demineralized water and/or water recycled from the process, especially rinse water.

The present invention is based on the finding that the polymer gel particles swell more significantly in the rinse water, and hence are more easily deformable and pass more easily through the openings of the separation unit. This unwanted swelling can be distinctly reduced by short dwell times. Moreover, the less swollen polymer gel particles can subsequently be dried more easily.

In a preferred embodiment of the present invention, the polymer gel obtained on the underside of the belt reactor is collected in a tank. Polymer gel adhering to the surface of the continuous belt can be detached solely by gravity or mechanically. In the case of mechanical detachment, this can be effected by a water jet and/or brushes.

The separation unit has openings for separation of the water. Suitable openings are the meshes of a screen and/or slots.

The meshes of the screen have a mesh size of at least 1 mm, preferably at least 1.5 mm, more preferably at least 2 mm, most preferably at least 3 mm. The mesh size should not exceed 15 mm.

The slots have a width of at least 1 mm, preferably at least 1.5 mm, more preferably at least 2 mm, most preferably at least 3 mm. The width of the slots should not exceed 15 mm. The position of the slots is not subject to any restriction and is, for example, in the range from 20 to 100 mm. Excessively long slots are disadvantageous for mechanical stability of the separation unit.

In a preferred embodiment of the present invention, the separation unit is a horizontal rotating drum, and the drum is inclined from the inlet to the outlet. The water is supplied here with the polymer gel at the upper end of the drum. The water can drain off through the openings in the wall of the drum, and the polymer gel leaves the drum at the lower end. The polymer gel separated off is recycled into the extruder after the polymerization.

The horizontal rotating drum is inclined relative to the horizontal by preferably at least 10°, more preferably at least 20°, most preferably at least 30°.

The water obtained in step iv) can be recycled into the process in step iii).

Together with the polymer gel recycled in step v), it is also possible in the process to recycle separated excessively small polymer particles ("fines") or add further additives.

The production of the superabsorbents is described in detail hereinafter:

The superabsorbents are produced by polymerizing a monomer solution and are typically water-insoluble.

The monomers a) are preferably water-soluble, i.e. their solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 02/055469 A1, WO 03/078378 A1 and WO 2004/035514 A1. A suitable monomer a) is, for example, an acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 03/104299 A1, WO 03/104300 A1, WO 03/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 02/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or propoxylated glycerols which have been esterified with acrylic acid or methacrylic acid to give di- or triacrylates, as described, for example, in WO 03/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05% to 1.5% by weight, more preferably 0.1% to 0.8% by weight and most preferably 0.15% to 0.5% by weight, calculated in each case on the basis of the total amount of monomer a) used. With rising crosslinker content, centrifuge retention capacity (CRC) falls and the absorption under a pressure of 21.0 g/cm$^2$ passes through a maximum.

Initiators c) used may be all compounds which generate free radicals under the polymerization conditions, for example thermal initiators, redox initiators or photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is preferably the disodium salt of 2-hydroxy-2-sulfonatoacetic acid or a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methyl cellulose or hydroxyethyl cellulose, gelatin, polyglycols or polyacrylic acids, preferably starch, starch derivatives and modified cellulose.

Typically, an aqueous monomer solution is used. The water content of the monomer solution is preferably from 40% to 75% by weight, more preferably from 45% to 70% by weight and most preferably from 50% to 65% by weight. It is also possible to use monomer suspensions, i.e. monomer solutions with monomer a) over and above the solubility, for example sodium acrylate. As the water content rises, the energy expenditure in the subsequent drying rises and, as the water content falls, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Polymerization on the belt is described, for example, in DE 38 25 366 A1 and U.S. Pat. No. 6,241,928. Polymerization in a belt reactor forms a polymer gel which has to be comminuted, for example in an extruder or kneader.

To improve the drying properties, the comminuted polymer gel obtained by means of a kneader can additionally be extruded.

The acid groups of the resulting polymer gels have typically been partly neutralized. Neutralization is preferably carried out at the monomer stage. This is typically accomplished by mixing in the neutralizing agent as an aqueous solution or else preferably as a solid. The degree of neutralization is preferably from 25 to 85 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof. Solid carbonates and hydrogencarbonates can also be introduced here in encapsulated form, preferably into the monomer solution directly prior to the polymerization, into the polymer gel during or after the polymerization and prior to the drying thereof. The encapsulation is effected by coating of the surface with an insoluble or only gradually soluble material (for example by means of film-forming polymers, of inert inorganic materials or of fusible organic materials) which delays the dissolution and reaction of the solid carbonate or hydrogencarbonate to such a degree that carbon dioxide is not released until during the drying and the superabsorbent formed has high internal porosity.

Optionally, a surfactant can be added to the monomer solution before the polymerization and the monomer solution can then be foamed with an inert gas or water vapor or by vigorous stirring. The surfactant may be anionic, cationic, zwitterionic or else nonionic. Preference is given to using a skin-friendly surfactant.

The polymer gel is then typically dried with an air circulation belt drier until the residual moisture content is preferably 0.5 to 10% by weight, more preferably 1 to 6% by weight and most preferably 1.5 to 4% by weight, the residual moisture content being determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the polymer gel before the drying is preferably from 25% to 90% by weight, more preferably from 35% to 70% by weight, most preferably from 40% to 60% by weight. Subsequently, the dried polymer gel is crushed and optionally coarsely comminuted.

Thereafter, the dried polymer gel is typically ground and classified, and the apparatus used for grinding may typically be single- or multistage roll mills, preferably two- or three-stage roll mills, pin mills, hammer mills or vibratory mills.

The average particle size of the polymer particles removed as the product fraction is preferably from 150 to 850 μm, more preferably from 250 to 600 μm, very particularly from 300 to 500 μm. The average particle size of the product fraction may be determined by means of EDANA recommended test method No. WSP 220.2-05 "Particle Size Distribution", where the proportions by mass of the screen fractions are plotted in cumulated form and the average particle size is determined graphically. The average particle size here is the value of the mesh size which arises for a cumulative 50% by weight.

The proportion of polymer particles having a particle size of greater than 150 μm is preferably at least 90% by weight, more preferably at least 95% by weight, most preferably at least 98% by weight.

Polymer particles with too small a particle size lower the gel bed permeability (GBP). The proportion of excessively small polymer particles ("fines") should therefore be small.

Excessively small polymer particles are therefore typically removed and recycled into the process, preferably immediately after the polymerization, i.e. prior to the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

The proportion of polymer particles having a particle size of at most 850 µm is preferably at least 90% by weight, more preferably at least 95% by weight, most preferably at least 98% by weight.

The proportion of polymer particles having a particle size of at most 600 µm is preferably at least 90% by weight, more preferably at least 95% by weight, most preferably at least 98% by weight.

Polymer particles of excessively large particle size lower the free swell rate. The proportion of excessively large polymer particles should therefore likewise be low. Excessively large polymer particles are therefore typically removed and recycled into the grinding.

To further improve the properties, the polymer particles can be thermally surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amido acetals in DE 103 34 584 A1, oxetanes and cyclic ureas in EP 1 199 327 A2 and morpholine-2,3-dione and derivatives thereof in WO 03/031482 A1.

Preferred surface postcrosslinkers are ethylene carbonate, ethylene glycol diglycidyl ether, reaction products of polyamides with epichlorohydrin and mixtures of propylene glycol and butane-1,4-diol.

Very particularly preferred surface postcrosslinkers are 2-hydroxyethyl-2-oxazolidinone, 2-oxazolidinone and propane-1,3-diol.

In addition, it is also possible to use surface postcrosslinkers which comprise additional polymerizable ethylenically unsaturated groups, as described in DE 37 13 601 A1.

The amount of surface postcrosslinker is preferably 0.001% to 3% by weight, more preferably 0.02% to 1% by weight and most preferably 0.05% to 0.2% by weight, based in each case on the polymer particles.

The surface postcrosslinking is typically performed in such a way that a solution of the surface postcrosslinker is sprayed onto the dried polymer particles. After the spray application, the polymer particles coated with surface postcrosslinker are surface postcrosslinked and dried, and the surface postcrosslinking reaction can take place both before and during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers have a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting characteristics and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The surface postcrosslinking is preferably performed in contact dryers, more preferably paddle dryers, most preferably disk dryers. Suitable dryers are, for example, Hosokawa Bepex® Horizontal Paddle Dryer (Hosokawa Micron GmbH; Leingarten; Germany), Hosokawa Bepex® Disk Dryer (Hosokawa Micron GmbH; Leingarten; Germany), Holo-Flite® dryers (Metso Minerals Industries Inc.; Danville; USA) and Nara Paddle Dryer (NARA Machinery Europe; Frechen; Germany). Moreover, fluidized bed dryers may also be used.

The surface postcrosslinking can be effected in the mixer itself, by heating the jacket or blowing in warm air. Equally suitable is a downstream dryer, for example a tray dryer, a rotary tube oven or a heatable screw. It is particularly advantageous to effect mixing and thermal surface postcrosslinking in a fluidized bed dryer.

Preferred reaction temperatures are in the range of 100 to 250° C., preferably 110 to 220° C., more preferably 120 to 210° C., most preferably 130 to 200° C. The preferred dwell time at this temperature is preferably at least 10 minutes, more preferably at least 20 minutes, most preferably at least 30 minutes, and typically at most 60 minutes.

In a preferred embodiment of the present invention, the polymer particles are cooled after the surface postcrosslinking. The cooling is preferably performed in contact coolers, more preferably paddle coolers and most preferably disk coolers. Suitable coolers are, for example, Hosokawa Bepex® Horizontal Paddle Cooler (Hosokawa Micron GmbH; Leingarten; Germany), Hosokawa Bepex® Disc Cooler (Hosokawa Micron GmbH; Leingarten; Germany), Holo-Flite® coolers (Metso Minerals Industries Inc.; Danville; USA) and Nara Paddle Cooler (NARA Machinery Europe; Frechen; Germany). Moreover, fluidized bed coolers may also be used.

In the cooler, the polymer particles are cooled to preferably 40 to 90° C., more preferably 45 to 80° C., most preferably 50 to 70° C.

Subsequently, the surface postcrosslinked polymer particles can be classified again, with excessively small and/or excessively large polymer particles being removed and recycled into the process.

To further improve the properties, the surface postcrosslinked polymer particles can be coated or remoisturized.

The remoisturizing is preferably performed at 40 to 120° C., more preferably at 50 to 110° C., most preferably at 60 to 100° C. At excessively low temperatures the polymer particles tend to form lumps, and at higher temperatures water already evaporates to a noticeable degree. The amount of water used for remoisturizing is preferably from 1% to 10% by weight, more preferably from 2% to 8% by weight and most preferably from 3% to 5% by weight. The remoisturizing increases the mechanical stability of the polymer particles and reduces their tendency to static charging. The remoisturizing is advantageously performed in a cooler after the thermal surface postcrosslinking.

Suitable coatings for improving the swell rate and the gel bed permeability (GBP) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20. Suitable coatings for dust binding, for reducing the tendency to caking and for increasing the mechanical stability are polymer dispersions as described in EP 0 703 265 B1, and waxes as described in U.S. Pat. No. 5,840,321.

Subsequently, the coated and/or remoisturized polymer particles can be classified again, with removal of excessively small and/or excessively large polymer particles and recycling into the process.

The present invention further provides hygiene articles comprising superabsorbents produced by the process of the invention.

Methods:

The standard test methods described hereinafter and designated "WSP" are described in: "Standard Test Methods for the Nonwovens Industry", 2005 edition, published jointly by the Worldwide Strategic Partners EDANA (Avenue Eugene Plasky, 157, 1030 Brussels, Belgium, www.edana.org) and INDA (1100 Crescent Green, Suite 115, Cary, North Carolina 27518, USA, www.inda.org). This publication is obtainable both from EDANA and from INDA.

The measurements should, unless stated otherwise, be conducted at an ambient temperature of 23±2° C. and a relative air humidity of 50±10%. The water-absorbing polymer particles are mixed thoroughly before the measurement.

Solids Content

In order to determine the solids content (SC), the polymer gel is dried (to constant weight) in a drying cabinet at 180° C. for at least 3 hours. The solids content is the weight of the dried polymer gel divided by the starting weight.

Free Swell Capacity, Deionized Water

Free swell capacity in water ($FSC_{DIW}$) is determined analogously to EDANA recommended test method No. WSP 240.2-05 "Free Swell Capacity in Saline, Gravimetric Determination", by drying the polymer gel prior to the measurement, grinding it and sieving it to a particle size range from 150 μm to 850 μm, and conducting the measurement in demineralized water rather than in a 0.9% by weight saline solution. The teabag should be correspondingly enlarged in the case of higher swelling capacities.

EXAMPLES

In order to simulate continuous polymerization on a belt, a static polymerization was conducted in each case. In order to simulate the introduction of a rinse water laden with polymer gel into the separation unit, the polymer gel was applied to a coarse-mesh screen and rinsed through with water.

Example 1

1028 g of a 37.3% by weight aqueous sodium acrylate solution, 98 g of acrylic acid, 254 g of water and 0.30 g of 3-tuply ethoxylated glycerol triacrylate were weighed out in a 2000 ml metal beaker. The neutralization level was 75 mol %. The metal beaker was closed with Parafilm® and inertized with 150 l/h of nitrogen. During the inertizing, the monomer solution was cooled to 3° C. Subsequently, 6.47 g of a 10% by weight aqueous solution of sodium persulfate and 5.88 g of a 1% by weight aqueous solution of hydrogen peroxide were added successively.

The monomer solution was transferred by means of a funnel into a glass dish having a diameter of 190 mm. The glass dish was covered with a polymer film and likewise inertized with 150 l/h of nitrogen. In addition, the monomer solution in the glass dish was stirred by means of a magnetic stirrer bar. Subsequently, by means of a disposable syringe, 5.88 g of a 1% by weight aqueous solution of Brüggolite® FF6 (disodium salt of 2-hydroxy-2-sulfinatoacetic acid) was metered into the monomer solution. After the reaction had started, the magnetic stirrer was switched off.

After a reaction time of 30 minutes, the polymer gel was removed and comminuted with an extruder having a perforated plate (hole diameter 13 mm).

The resultant polymer gel had a solids content of 35.0% by weight.

A portion of the polymer gel was dried in an air circulation drying cabinet at 160° C. for one hour. The loading of the trays with polymer gel was 0.19 g/cm². Subsequently, comminution was effected with a roll mill in four stages with gap widths of 5 mm, 1000 μm, 600 μm and 400 μm, and the material was screened to a particle size of 150 μm to 850 μm. The free swell capacity ($FSC_{DIW}$) of the superabsorbent particles thus obtained was determined, which gave a value of 162 g/g.

Example 2

950 g of a 37.3% by weight aqueous sodium acrylate solution, 146 g of acrylic acid, 335 g of water and 0.63 g of 3-tuply ethoxylated glycerol triacrylate were weighed out in a 2000 ml metal beaker. The neutralization level was 65 mol %. The metal beaker was closed with Parafilm® and inertized with 150 l/h of nitrogen. During the inertizing, the monomer solution was cooled to 3° C. Subsequently, 6.47 g of a 10% by weight aqueous solution of sodium persulfate and 5.88 g of a 1% by weight aqueous solution of hydrogen peroxide were added successively.

The monomer solution was transferred by means of a funnel into a glass dish having a diameter of 190 mm. The glass dish was covered with a polymer film and likewise inertized with 150 l/h of nitrogen. In addition, the monomer solution in the glass dish was stirred by means of a magnetic stirrer bar. Subsequently, by means of a disposable syringe, 5.88 g of a 1% by weight aqueous solution of Brüggolite® FF6 (disodium salt of 2-hydroxy-2-sulfinatoacetic acid) was metered into the monomer solution. After the reaction had started, the magnetic stirrer was switched off.

After a reaction time of 30 minutes, the polymer gel was removed and comminuted with an extruder having a perforated plate (hole diameter 13 mm).

The resultant polymer gel had a solids content of 35.5% by weight.

A portion of the polymer gel was dried in an air circulation drying cabinet at 160° C. for one hour. The loading of the trays with polymer gel was 0.19 g/cm². Subsequently, comminution was effected with a roll mill in four stages with gap widths of 5 mm, 1000 µm, 600 µm and 400 µm, and the material was screened to a particle size of 150 µm to 850 µm. The free swell capacity ($FSC_{DIW}$) of the superabsorbent particles thus obtained was determined, which gave a value of 195 g/g.

Example 3

For each experiment, the amount of wet polymer gel used was weighed beforehand, and the solids content (SC) of the polymer gel was determined.

About 20 g in each case of polymer gel was not pre-swollen (swell time 0 minutes), and about 10 g in each case of polymer gel was pre-swollen in 2 l of deionized water for 3 minutes (swell time 3 minutes), 30 minutes (swell time 30 minutes) or 60 minutes (swell time 60 minutes).

Subsequently, the pre-swollen polymer gels, together with the water from the polyethylene beakers used, was poured in each case onto a screen construction composed of an upper, coarse-mesh screen (separation screen) and two close-mesh screens (auxiliary screens) beneath. The non-pre-swollen polymer gels were applied directly to the separation screen. The separation screens had respective mesh sizes of 2000 µm, 3550 µm and 5000 µm. The auxiliary screens had mesh sizes of 630 µm and 400 µm. The diameter was 20 cm in each case. The auxiliary screens served to determine the proportion of polymer gel that passed through the separation screens.

The polymer gels were each distributed homogeneously on the separation screen and then subjected to a water jet from a height of 11 cm (7.5 liters of demineralized water per minute; inner hose diameter 8 mm) for 40 seconds. The water jet hit the polymer gel on the screen over the course of the 40 seconds always in uniform movements in order to cover the total area in a comparable manner. Subsequently, the screens were placed over a bucket for 5 minutes for the water to drip off, then, for quantification, predried in an air circulation drying cabinet at 135° C. for 2 hours and finally dried under reduced pressure for about a further 16 hours. The mass of the dried polymer gel on the separation screen (yield) and that on the two auxiliary screens (loss) was determined and expressed as a percentage in table 1.

The results are compiled in table 1.

TABLE 1

Yield of polymer gel after separation

| Polymer gel | DN [mol %] | SC [% by wt.] | $FSC_{DIW}$ [g/g] | Separation screen [µm] | Swell time [min] | Yield [%] | Loss [%] |
|---|---|---|---|---|---|---|---|
| Ex. 1 | 75 | 35.0 | 162 | 2000 | 0 | 99.4 | 0.6 |
|  |  |  |  |  | 3 | 99.1 | 0.9 |
|  |  |  |  |  | 30 | 94.8 | 5.2 |
|  |  |  |  |  | 60 | 92.8 | 7.2 |
| Ex. 2 | 65 | 35.5 | 195 | 3550 | 0 | 100 | 0.0 |
|  |  |  |  |  | 3 | 100 | 0.0 |
|  |  |  |  |  | 30 | 94.3 | 5.7 |
|  |  |  |  |  | 60 | 88.9 | 11.1 |
| Ex. 2 | 65 | 35.5 | 195 | 5000 | 0 | 95.9 | 4.1 |
|  |  |  |  |  | 3 | 88.6 | 11.4 |
|  |  |  |  |  | 30 | 80.0 | 20.0 |
|  |  |  |  |  | 60 | 75.8 | 24.2 |

DN degree of neutralization
SC solids content

The examples show that the polymer gel can be separated off only incompletely with increasing dwell time in the rinse water.

The invention claimed is:

1. A process for producing superabsorbent particles by polymerizing a monomer solution comprising
    a) at least one ethylenically unsaturated monomer which bears an acid group and has been neutralized to an extent of 50 to 85 mol %,
    b) at least one crosslinker,
    c) at least one initiator,
    d) optionally one or more ethylenically unsaturated monomer copolymerizable with the monomers mentioned under a) and
    e) optionally one or more water-soluble polymer,
    comprising
    i) continuously polymerizing the monomer solution on a continuous belt of a belt reactor,
    ii) comminuting a polymer gel obtained in step i),
    iii) rinsing the polymer gel obtained on the underside of the belt reactor into a separation unit with water,
    iv) separating the polymer gel from the water in the separation unit and
    v) recycling the polymer gel separated off in step iv) into step ii),
    wherein the polymer gel has a swelling capacity in water of at least 100 g/g, a dwell time between step iii) and step iv) is less than 20 minutes, and the separation unit in step iv) has openings with a clear width of at least 1 mm.

2. The process according to claim 1, wherein the dwell time between step iii) and step iv) is less than 15 minutes.

3. The process according to claim 1, wherein the dwell time between step iii) and step iv) is less than 10 minutes.

4. The process according to claim 3, wherein the dwell time between step iii) and step iv) is less than 5 minutes.

5. The process according to claim 1, wherein the polymer gel obtained on the underside of the belt reactor is collected in a tank.

6. The process according to claim 1, wherein the separation unit in step iv) has openings having a clear width of at least 1.5 mm.

7. The process according to claim 6, wherein the separation unit in step iv) has openings having a clear width of at least 2 mm.

8. The process according to claim 7, wherein the separation unit in step iv) has openings having a clear width of at least 3 mm.

9. The process according to claim 1, wherein the openings in the separation unit in step iv) consist of the meshes of a screen.

10. The process according to claim 1, wherein the openings in the separation unit in step iv) take the form of slots.

11. The process according to claim 1, wherein the separation unit is a horizontal rotating drum, and the drum is inclined from the inlet to the outlet.

12. The process according to claim 11, wherein the drum is inclined by at least 10° relative to the horizontal.

13. The process according to claim 12, wherein the drum is inclined by at least 20° relative to the horizontal.

14. The process according to claim 13, wherein the drum is inclined by at least 30° relative to the horizontal.

15. The process according to claim 1, wherein water obtained in step v) is recycled into the process in step iii).

16. A hygiene article comprising superabsorbents produced by a process of claim 1.

* * * * *